United States Patent [19]

Hogrefe et al.

[11] Patent Number: 5,415,181
[45] Date of Patent: May 16, 1995

[54] AM/FM MULTI-CHANNEL IMPLANTABLE/INGESTIBLE BIOMEDICAL MONITORING TELEMETRY SYSTEM

[75] Inventors: Arthur F. Hogrefe, Laurel; Jeffery C. Lesho, Brookville; Harry A. C. Eaton, Columbia, all of Md.

[73] Assignee: The Johns Hopkins University, Baltimore, Md.

[21] Appl. No.: 160,716

[22] Filed: Dec. 1, 1993

[51] Int. Cl.$^6$ .............................................. A61B 5/00
[52] U.S. Cl. .................................... 128/736; 128/903; 128/630
[58] Field of Search ................ 128/903, 736, 630–631; 607/60

[56] References Cited

U.S. PATENT DOCUMENTS

| | | |
|---|---|---|
| 2,233,183 | 2/1941 | Roder . |
| 2,237,522 | 4/1941 | Clark . |
| 2,675,540 | 4/1954 | Schultheis . |
| 3,188,615 | 6/1965 | Wilcox . |
| 3,210,747 | 10/1965 | Clynex . |
| 3,500,248 | 3/1967 | Stratman . |
| 3,572,316 | 2/1968 | Vogelman et al. . |
| 3,682,160 | 8/1972 | Murata . |
| 3,717,857 | 2/1973 | Evans . |
| 3,971,362 | 7/1976 | Pope et al. ................ 128/736 X |
| 4,017,810 | 4/1977 | Vahaviolos . |
| 4,053,951 | 10/1977 | Hudspeth et al. . |
| 4,110,708 | 8/1978 | Mendenhall . |
| 4,177,800 | 12/1979 | Enger . |
| 4,259,744 | 3/1981 | Junod et al. . |
| 4,356,486 | 10/1982 | Mount ......................... 128/903 X |
| 4,475,823 | 10/1984 | Stone . |
| 4,494,553 | 1/1985 | Sciarra et al. . |
| 4,528,637 | 7/1985 | Smith . |
| 4,603,306 | 7/1986 | Kleinberg . |
| 4,686,998 | 8/1987 | Robbins ....................... 128/903 X |
| 4,719,432 | 1/1988 | Heck et al. . |
| 4,746,879 | 5/1988 | Ma et al. . |
| 4,761,539 | 8/1988 | Carmean . |
| 4,844,076 | 7/1989 | Lesho et al. . |
| 4,901,257 | 2/1990 | Chang et al. . |
| 4,908,760 | 3/1990 | Sinn . |
| 4,931,967 | 6/1990 | Boe et al. . |
| 4,944,299 | 7/1990 | Silvian . |

OTHER PUBLICATIONS

Lindqvist; WO89/01722; Feb. 1989.
Voegeli et al.; "Multichannel Telemetry of Physiological Parameters in the Rat"; Conf: Int'l Symp. on Biotelemetry; Netherlands; May 1971, pp. 371–380.
Freund et al.; "Miniature Multi-Channel Telemetry System For Physiological Monitoring"; Conf.-Proc. Of The 26th Ann. Conf. on Engin. in Med. & Biol.; Oct. 1973, p. 7.
Ivison et al.; "Digital Phase Modul. and Demod. For A Biomed. Telemetry System"; Med. And Biol. Engineering; Jan. 1974; vol. 12, No. 1; pp. 109–112.

*Primary Examiner*—Angela D. Sykes
*Attorney, Agent, or Firm*—Eugene J. Pawlikowski

[57] ABSTRACT

A multi-channel circuit for telemetering signals representing physiological values from a point in a human body to a receiver (24) outside of the body. The two signals ($S_1$, $S_2$) other than the temperature signal (27') are used to provide two frequency modulated signals (14, 16) summed by an amplifier (18) with the summed FM signal then being applied to amplitude modulate (21) a carrier (8) whose frequency varies as a function of temperature. The resulting FM/AM signal (22) is telemetered inductively outside of the body to an external receiver (24). Appropriate demodulation, filter, and shaping circuits within the external circuit detect the FM signals (14, 16) and thus produce three independent frequencies two of which are the original physiological variables and the third a function of local temperature. Real time plot of the two physiological variables can be obtained using FM discriminators while the temperature dependent frequency is best monitored by a counter.

21 Claims, 3 Drawing Sheets

AM/FM MULTI-CHANNEL IMPLANTABLE/INGESTIBLE BIOMEDICAL MONITORING TELEMETRY SYSTEM

STATEMENT OF GOVERNMENTAL INTEREST

The Government has rights in this invention pursuant to Contract No. N00039-91-C-0001 awarded by the Department of the Navy.

BACKGROUND OF THE INVENTION

1. Field of the Invention

The invention relates to a multi-channel implantable/ingestible telemetry system which offers major improvements in the electronic design of data links for biomedical or industrial use. More particularly, the design parameters for the telemetry system of the invention may be incorporated in a miniaturized multi-channel implantable/ingestible capsule for generating signals representing various physiological stimuli and capable of extremely stable DC signal measurement capability, low power consumption for all channels, insensitivity to battery voltage variation, and size for low cost in fabrication and manufacture.

2. Description of the Prior Art

Several examples of technologies that have already been implemented or seen experimentation within the context of implantable/ingestible devices include such devices as an implantable temperature monitor for the heart, commandable temperature capsules which transmit signals only in response to request for transmission, rechargeable/reusable capsules for animal work, and certain experimental designs for pill identification or calibration. Efforts have also been directed to gastrointestinal applications as, for example, monitoring $CO_2$ in the gut in which case preferable design requirements include the ability to provide intermittent transmission and automatic shut-off at the end of useful life.

Therefore, there is the need, not taught in the prior art, for a completely designed and tested telemetry system having commercial as well as biomedical applications but principally intended for implantation into or ingestion by a human subject and offering flexibility and reliability when measuring parameters within the human environment with a minimum of interference therebetween.

Accordingly, an object of the invention is a multi-channel device for collecting, amplifying and converting to useable information biological signals representative of a plurality of physical stimuli.

Another object of the invention is to fabricate a two-part system which inductively reads out from a controlled body environment a plurality of physiological signals.

A further object of the invention is to provide an implantable pill which has three independent channels for developing information from implanted sensors without interference.

Still a further object of the invention is to provide carrier and subcarrier modulation from voltage control oscillators having substantially no overlap or interference with each other in the course of generating a plurality of signals indicative of a human condition.

Yet a further object of the invention is the design of receiver electronics which can in principle be interfaced to biomedical long-range communication technologies such as cellular phones, or radio, to effect long-range telemetry.

SUMMARY OF THE INVENTION

The present invention comprises a multi-channel modulation circuit that has been uniquely designed to propagate at least two physiological signals from points in a human body to a receiver outside of the human body and, in addition, transmit simultaneously a signal representative of body temperature. The two signals other than the signal representing the measured temperature can be any mechanically generated or biological signal that can fit into a prescribed channel bandwidth. In the preferred embodiment, two voltage controlled oscillators receive two conditioned biomedical signals and use them to frequency modulate two subcarriers separated in frequency by a ratio of at least 5-1. The two FM channels are summed by an amplifier and the result is applied to amplitude modulate a 262 kHz temperature channel carrier whose frequency varies as a function of body temperature. The resulting AM signal is telemetered outside of the body via magnetic induction to the pickup coil of an external receiver. The external receiver is equipped with an automatic gain control to prevent the receiver/amplifier from limiting and thus distorting the amplitude modulated signal. At the receiver, an AM demodulator produces the sum of the two FM signals and the temperature signal is separately demodulated. The two FM signals are separated using filters. The two independent FM signals are then demodulated using phase lock loops. The decoded FM signals are then filtered to obtain the best signal-to-noise ratio. The system thus produces three distinct output signals each representing a physiological variable in the body.

Other objects of the invention will become apparent from the following detailed description of embodiments of the present invention when taken in conjunction with the accompanying drawings.

DETAILED DESCRIPTION OF THE PREFERRED EMBODIMENT

Figure 1:
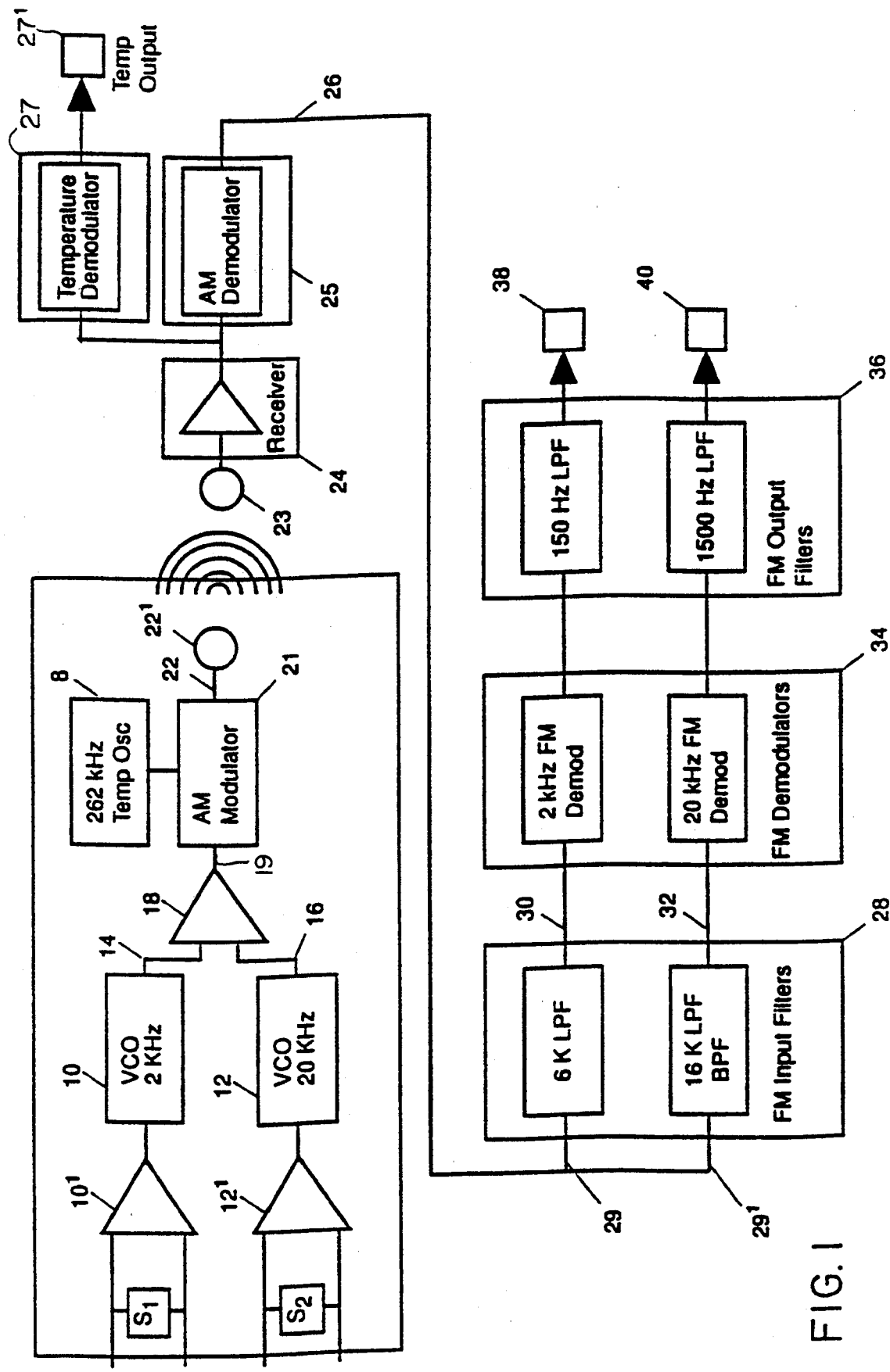
FIG. 1 is a schematic drawing of the present invention of a multi-channel telemetry circuit for measuring multiple signals.

Referring to FIG. 1, the multi-channel monitoring system modulation and telemetry circuit of the present invention adapted for transmitting electrical signals corresponding to physiological measurements made in a human body is uniquely designed to telemeter from one point to a second remote point at least two signals each of which represents a physiological variable measured in conjunction with a simultaneously developed temperature signal. To illustrate the invention in its simplest possible form, it will be assumed that the telemetering system is intended to transmit three signals two of which are derived from sensors $S_1$ and $S_2$ and the third being generated by an oscillator 8 whose output signal concerns body temperature. The sensors $S_1$ and $S_2$ may be of any known form for biological or non-biological purposes.

As indicated, signals $S_1$ and $S_2$ are intended to represent two distinct biological features occurring within a preselected bandwidth which may range, for example, approximately between 0 and 150 Hz and 0 and 1500 Hz. Positioned within an enclosure generally designated 9, are two voltage controlled oscillators 10, 12 which receive, after conditioning and shaping by circuits 10' and 12', the two input signals $S_1$ and $S_2$. The conditioned and shaped input signals $S_1$ and $S_2$ frequency modulate the oscillators 10 and 12 which, for example, as illustrated in FIG. 1, have frequencies of approximately 2 kHz and 20 kHz, respectively. The two FM subcarrier signals 14, 16 are summed by an amplifier 18 and the combination FM signal is used by modulator 21 to amplitude modulate the signal from oscillator 8 which acts as a carrier. The frequency of oscillator 8 varies as a function of temperature. In a preferred embodiment, oscillator 8 contains a Statek TS-2 timing fork (not shown) having a center frequency of approximately 262 kHz and a transfer function of approximately 9 Hz shift per °C. change in temperature. One example of the operation of oscillator 8 may be found in the co-pending patent application Ser. No. 08/016,350 filed on Feb. 11, 1993 and having a common assignee. The frequency modulated signals in channels 14 and 16 may conveniently be summed in amplifier 18 because they are distinct in the frequency domain.

The resultant amplitude modulated signal on line 22 is propagated via magnetic induction by output coil 22' to an external pick-up coil 23 which serves as the input of a receiver 24 outside the human body. Receiver 24 amplifies the signal received from the external coil 23 and must be equipped with automatic gain control to prevent the receiver/amplifier from limiting and thus distorting the AM signal. An AM detector 25 produces on line 26 the sum of the two FM signals originally present in the form of signals at 19. At the same time, the temperature dependent signal produced at oscillator 8 is separately demodulated by demodulator 27 and registered in a recorder 27' for indicating the temperature. The reconstructed FM signals on line 26 are separated in a filter box 28 by op-amp filters. Conveniently shown as the filters are a 6K low pass filter in the low frequency or upper output channel 29 and a 16K–24K bandpass filter shown in the high frequency or lower output channel 29'. The separated FM signals which appear on lines 30, 32 are demodulated using phase locked loops (not shown) in an FM demodulator box 34 so that the output signals of demodulators 34 are faithful replicas of the input signals $S_1$ and $S_2$. The two output signals of the FM demodulator box 34 are further conditioned in a FM output filter box 36 to optimize the signal-to-noise ratio. A range found suitable for the bandwidth of the FM output filter 36 is 150 Hz–1500 Hz, as shown, thus matching the original signal spectrum. Receivers 38 and 40, respectively, record the value of the physiological or biomedical signals produced as the output of the FM output filters 36.

Figure 2:
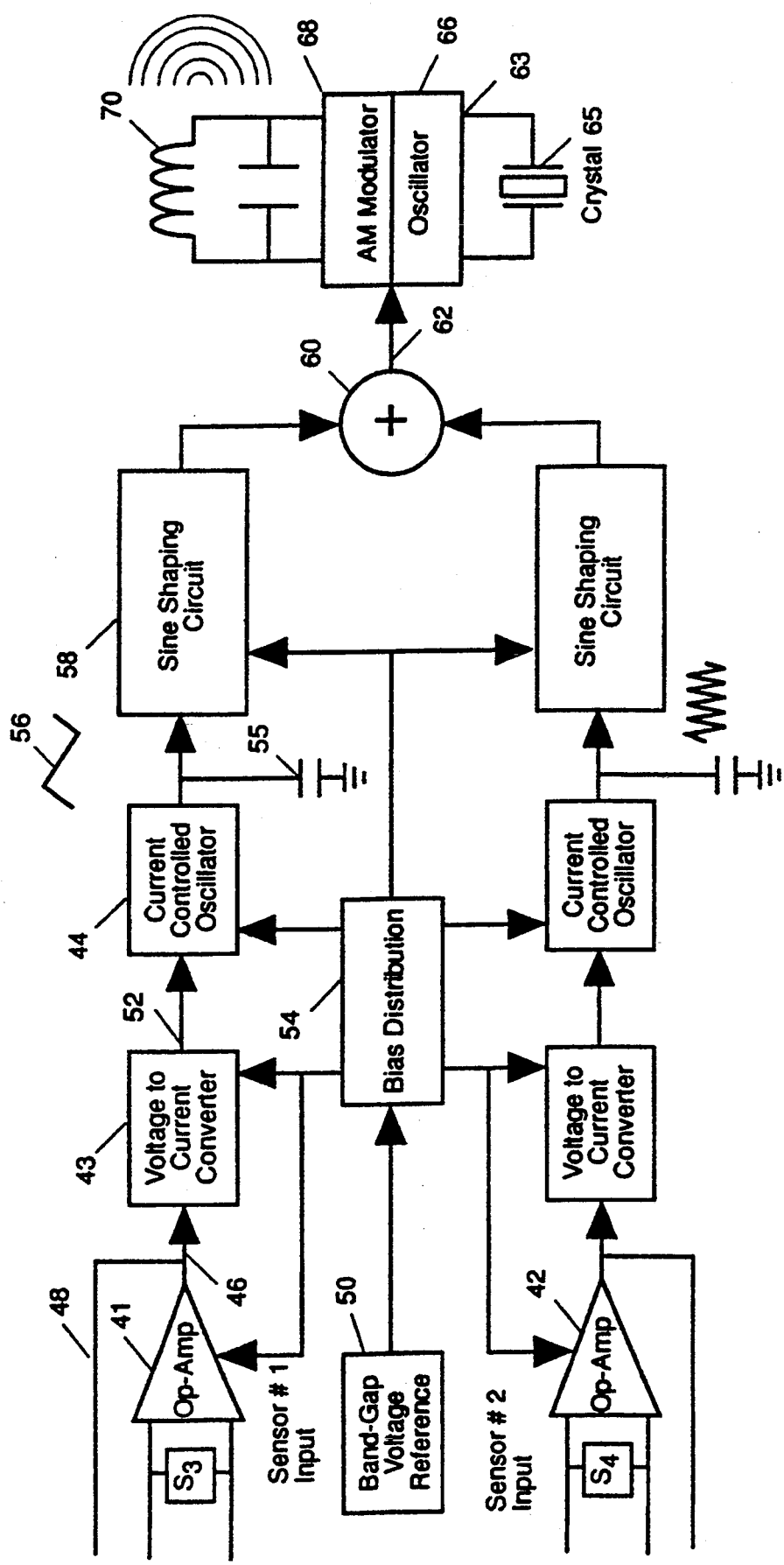
FIG. 2 is a schematic diagram of a second embodiment of the invention using sine shaping circuits as a means to reduce cross-talk between two subcarriers and to allow greater flexibility in choosing the subcarrier channel assignments.

Turning now to the three-channel telemetry system of the invention as embodied in FIG. 2, the system is arranged to transmit signals over three channels much in the same manner as described in connection with FIG. 1 but with several important differences related mainly to the formation of signals within the transmitter portion of the system. As shown in FIG. 2, a low frequency channel is characterized as having an input signals $S_3$ which is applied to an op-amp 41 band limited, for example, from 0 to 250 Hz. A high frequency channel supplied with an input signal $S_4$ is characterized by an op-amp 42 band limited from 0 to 1300 Hz. As already described in connection with FIG. 1, the FIG. 2 embodiment employs a combination of frequency modulation and amplitude modulation functions to fulfill a need in diagnostic medicine to measure physiological variables at the point of origin within a human body without prolonged invasive procedures. It will be understood, therefore, that only the operation of the low frequency or upper channel in FIG. 2 will be described as the two channels downstream of the op-amps 41 and 42 operate identically and differ from each other only in the center frequency of their respective current controlled oscillators.

The sensor input $S_3$ to the low frequency or upper channel is amplified and conditioned by op-amp 41. The input transistor in the op-amp is a MOSFET and so it has inherently high input impedance and low bias current. The amplified sensor signal from op-amp 41 is converted to a current by means of a voltage to current converter 43 to drive a current controlled oscillator 44. The voltage to current converter 43 has a differential input between terminals 46 and 48 thereof whose form depends upon the interface between the op-amp 41 and the physiological junction under observation. In a typical case, and as shown herein, the voltage to current converter 43 is provided with a positive lead 46 internally connected to the op-amp output and a negative lead 48 available for user connection to a reference point.

The input to the voltage to current converter 43 is also a high impedance MOSFET input. The differential input voltage into converter 43 is driven across an on-chip 100K $\Omega$ resistor (not shown) to produce an output current fed to the current controlled oscillator 44. A fixed offset current (nominally 10 $\mu$A) derived from a band-gap voltage reference 50 is added to line 52 from a bias distribution 54. The offset current, when combined with the differential input to voltage to current converter 43 between terminals 46 and 48, sets the center frequency of the current controlled oscillator 44 thus allowing both positive and negative deviations of the differential voltage input.

The current into the current controlled oscillator 44 programs the magnitude of the current through an external capacitor 55. The capacitor 55 is thus charged and discharged between two fixed voltages. When the voltage on capacitor 55 reaches one of the voltage trip points, the direction of the capacitor current is reversed as shown in FIG. 2 by the waveform 56. The resulting output of the current controlled oscillator 44 is a triangular wave which varies between two voltages (nominally 400 mV and 800 mV) as established by the band-gap voltage reference 50. It has been found that using voltages from the bias distribution 54 and referencing them to the band-gap voltage reference 50 advantageously reduces sensitivity to both supply voltage and temperature variations.

The instantaneous frequency of the current controlled oscillator 44 may be described by equation 1:

$$(f = 1.0 + Vd)/(0.8\ RC) \tag{1}$$

where Vd is the differential voltage between terminals 46 and 48 at the input of voltage to current converter 43, R is 100 kΩ and C is the value of the external capacitor 54. Equation 1 shows that the signal of interest frequency modulates the waveform of the current controlled oscillator 44. The frequency modulation of the sensor input at op-amp 41 allows constant voltages to be measured. In addition, the current controlled oscillators are designed for wide-band fm modulation in order to maintain dc accuracy. Constant voltages or currents may be produced by a variety of sensors including strain gauges, chemical sensors and others.

The triangular wave 56 from the current controlled oscillator 44 contains odd harmonics of the fundamental frequency of oscillator 44. It is recognized that the harmonics from the low frequency or upper channel may fall into the band allocated to the high frequency or lower channel and may cause interference problems. To minimize such interference, the low frequency or upper channel shown in FIG. 2 has the developed signal passing through a sine shaping circuit 58. The sine shaping circuit 58 shown in FIG. 2 substantially attenuates the odd harmonics present in the triangular wave 56 and is preferably employed because it uses much less chip area than filter circuits, requires no external parts, and provides maximum flexibility for configuring the sub-carrier channels.

In the summing amplifier 60, the two shaped signals from the low and high frequency channels are summed to produce a combined signal on line 62 that contains all of the desirable information from the two sensor inputs at op-amps 41. The signals from sine shaping circuits 58 can conveniently be summed because the center frequencies of the current controlled oscillators and frequency deviations are chosen to limit the amount of cross talk between the low and high frequency channels.

As further shown in FIG. 2, a third channel generally designated 63 is dedicated to measurement of the physiological temperature of importance during an examination or experiments involving a subject, whether human or animal. The transducer in the channel 63 is a temperature sensitive crystal 65 which swings the frequency of an oscillator 66 about a base frequency of approximately about 262 kHz. The output of oscillator 66 is amplitude modulated in AM modulator 68 by the output of summing amplifier 60. The final signal, which contains two FM signals amplitude modulated onto the temperature signal, drives a small coil 70 that transmits the signal. The coil 70 generates a magnetic field that is inductively coupled to an external receiver not shown in FIG. 2, but understood to be similar in form and function to the external receiver described in connection with the embodiment shown in FIG. 1. In practice, the temperature sensing crystal 65 used to generate the AM carrier resonates at approximately 262 kHz at 25° C. and nominally varies 9 Hz/°C. In practice, the temperature measurement can be calibrated to better than 0.1° C.

Accordingly, although not shown in the FIG. 2 embodiment, it will be understood that the signal transmitted by the coil 70 is picked up by an external receiver coil, amplified appropriately, and directed over three separate paths, one for the temperature signal, and one each for the biological inputs sensed at the op-amps 41. As further will be understood from the description of FIG. 1, the signals produced by the low and high frequency channels are generated by demodulating the signals produced by the current controlled oscillators 44. Band pass filters are used to extract the individual FM channel signals. The separated signals are then individually FM demodulated by phase lock loop circuits. A final filter to remove the FM carrier frequencies provides the two measured physiological variables. Appropriate demodulation occurs simultaneously to produce a signal proportional to the temperature affecting the crystal 65 in oscillator 66. It will thus be understood that the demodulation products of the receiver actively associated with the invention embodiment shown in FIG. 2 are faithful replicas of the input signals $S_3$ and $S_4$ and the output of oscillator 66.

Figure 3:
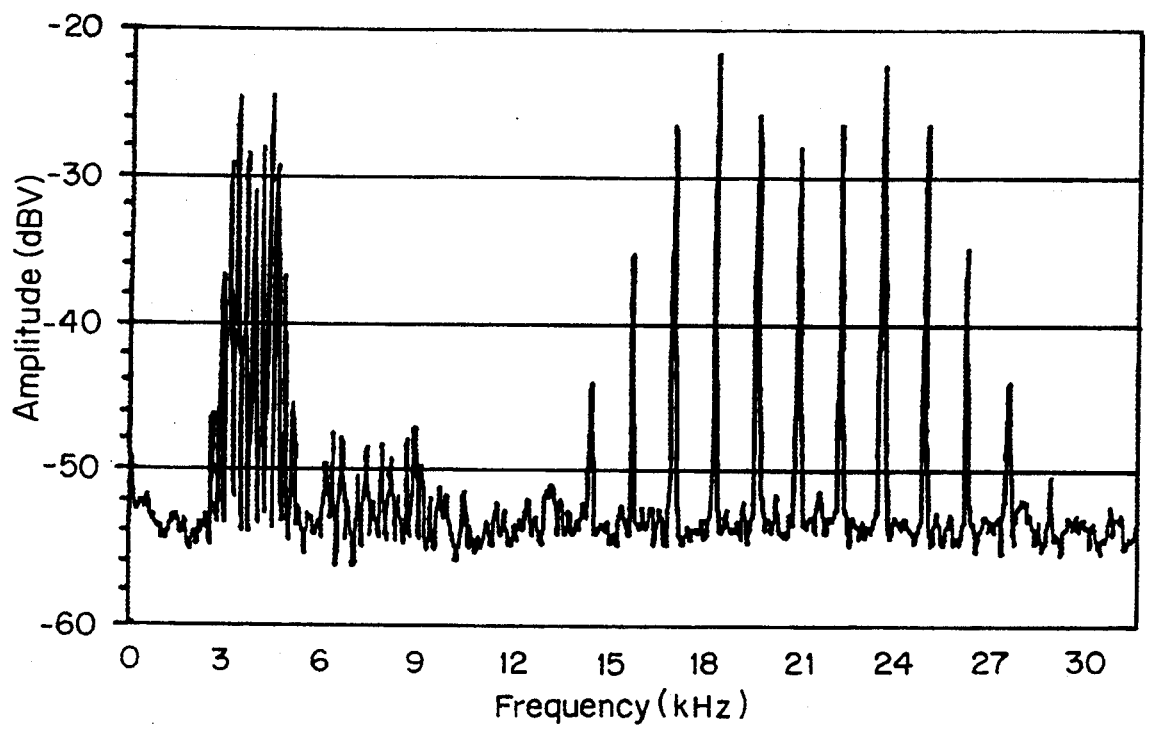
FIG. 3 shows a frequency spectrum for summed FM channels under maximum bandwidth conditions in accordance with the invention.

With reference now to FIG. 3, the center frequencies of the current controlled oscillators 44 shown in FIG. 2 are determined by the nominal bias point of the input amplifier, the voltage to current converter reference voltage, the offset current, and the external capacitor. The offset current is determined by the band-gap voltage and an on-chip resistor. Because of the wide variation (±30%) in the absolute value of the on-chip resistors, the current controlled oscillator output capacitors generally have to be selected or trimmed in order to accurately set the center frequencies of the current controlled oscillators. Trimming the center frequency also trims the frequency sensitivity of the current controlled oscillator because the voltage to current converter uses an on-chip resistor that is matched to the resistor that sets the offset current. Applications that require low dynamic range and limited signal voltage may be able to use fixed value capacitors at the outputs of the current controlled oscillators. For wide bandwidth applications, it has been found that the maximum frequency deviation of the current controlled oscillators should be around ±20% of the center frequency. This range allows the second harmonic caused by distortion in the sine-shaper and receiver circuits to fall outside of the passband of the FM signal, while still allowing for reasonable dc accuracy. Using ±20% frequency deviation allows a total frequency error of 0.4% not related to the input signal while maintaining a 1% of full scale dc accuracy. Many different channel assignments are possible for this device. One test system uses center frequencies at 3.8 kHz and 20 kHz. When modulated with maximum amplitude (≧ frequency deviation), maximum frequency (250 Hz and 1.3 kHz) inputs (corresponding to maximum channel bandwidth conditions) the measured frequency spectrum for the summed signal shown in FIG. 3 results. Second harmonic distortion from the sine shaping circuit appears as a weak signal that falls between the passbands assigned to the low and high frequency channels. The sine shaping circuit minimizes the third and fifth harmonics in order to keep cross-talk to a minimum. Allowing larger than 20% frequency deviation can improve the dc accuracy, because this tends to reduce the relative importance of battery voltage, and temperature on the center frequency. If the maximum frequency deviation is raised much beyond the 20% level there will still be little cross-talk, but the second harmonic distortion will fall into the signal's own passband resulting in distortion. This is not a problem for dc signals, and is unimportant if the amplitude of high frequency inputs is small.

Figure 4:
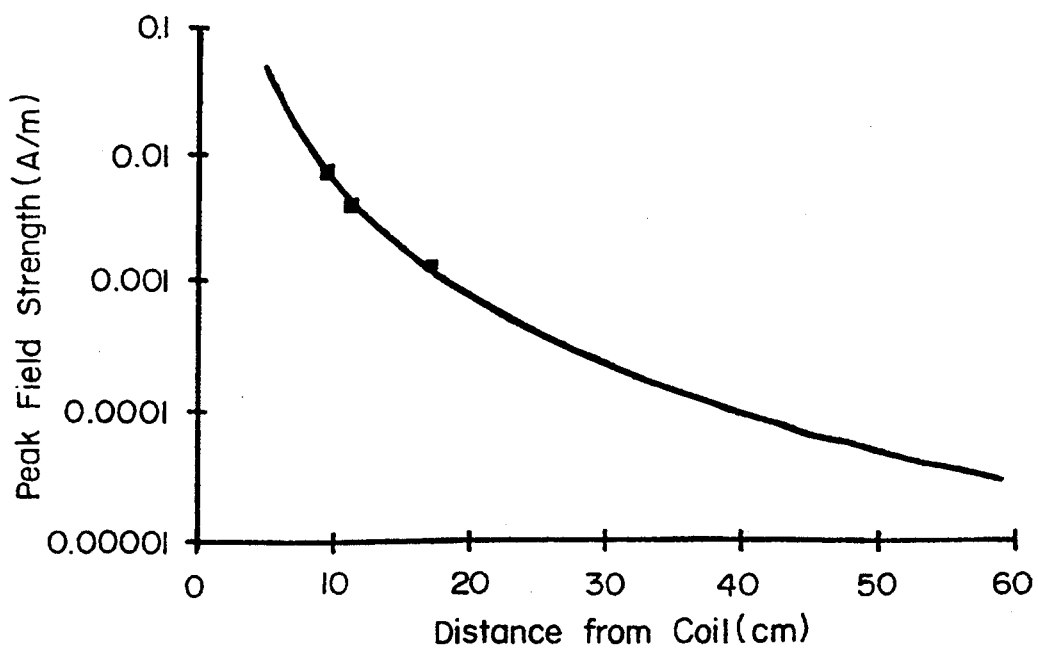
FIG. 4 is a diagram showing the peak field strength versus distance from a coil in centimeters in a typical commercial environment according to the invention.

FIG. 4 shows the peak field strength of the transmitted signal from a coil having 300 turns in four layers 8.6 mm in diameter by 8.6 mm tall. The transmitter was operating with a nominal 3 V power supply. Range in a typical commercial environment is greater than 60 cm. Strong interfering signals can reduce the usable range. The transmitting coil current and field strength are proportional to supply voltage. This feature allows the power drain on the battery to diminish as the battery voltage falls resulting in slightly longer battery life. The test coil used in this measurement is applicable to ingestible applications where the telemetry system is packaged in a capsule form. Many other coil arrangements for different applications are possible.

While certain representative embodiments of the invention have been shown and described for the purpose of illustrating the invention, it will be apparent to those skilled in the art that various changes and modifications may be made therein without departing from the spirit and scope of the invention.

We claim:

1. A system for propagating a plurality of signals indicative of physiological stimuli from a point inside a human body to a point external to the body comprising:
   a. first sensor means responsive to a first physiological stimulus for producing a first signal;
   b. second sensor means responsive to a second physiological stimulus for producing a second signal;
   c. a first oscillator modulated by said first signal and having a frequency depending on the instantaneous amplitude of said first signal;
   d. a second oscillator modulated by said second signal and having a frequency dependent on the instantaneous amplitude of said second signal;
   e. said first and second oscillators having two different subcarrier frequencies;
   f. means for summing the output signals of said oscillators thereby producing a third signal;
   g. temperature responsive means for independently of said first and second oscillators producing a fourth signal which varies in frequency as a function of body temperature;
   h. modulator means coupled to the outputs of said summing means and said temperature responsive means for modulating said fourth signal by said third signal thereby producing a fifth signal which contains information of said first, second, and fourth signals;
   i. means for propagating said fifth signal to a point external of said human body; and
   j. receiver means intercepting said fifth signal for separating said first, second, and fourth signals from each other thereby providing means for indicating said physiological stimuli and said body temperature.

2. A system defined by claim 1, wherein said first and second signals lie within a bandwidth of approximately 0–150 Hz and 0–1500 Hz, respectively.

3. A system defined by claim 1, wherein said first and second oscillators have subcarrier frequencies of approximately 2 kHz and 20 kHz, respectively.

4. A system defined by claim 1, wherein said summing means is an amplifier.

5. A system defined by claim 1, wherein said temperature responsive means includes an oscillator whose center frequency is approximately 262 kHz.

6. A system defined by claim 1, wherein said modulator means comprises an amplitude modulator.

7. A system defined by claim 5, wherein said temperature responsive means has a transfer function of approximately 9 Hz shift per °C. change in temperature.

8. A system defined by claim 1, wherein said receiver means comprises first and second demodulating circuits to produce replicas of said first and second signals and said fourth signal.

9. A system for propagating a plurality of signals indicative of physiological stimuli from a point inside a human body to a point external to the body comprising:
   a. first sensor means responsive to a first physiological stimulus for producing a first signal;
   b. second sensor means responsive to a second physiological stimulus for producing a second signal;
   c. a first oscillator modulated by said first signal and having a frequency depending on the instantaneous amplitude of said first signal;
   d. a second oscillator modulated by said second signal and having a frequency dependent on the instantaneous amplitude of said second signal;
   e. said first and second oscillators having two different subcarrier frequencies;
   f. means for summing the output signals of said oscillators thereby producing a third signal;
   g. temperature responsive means for independently of said first and second oscillators producing a fourth signal which varies in frequency as a function of body temperature;
   h. modulator means coupled to the outputs of said summing means and said temperature responsive means for modulating said fourth signal by said third signal thereby producing a fifth signal which contains information of said first, second, and fourth signals;
   i. means for propagating said fifth signal to a point external of said human body; and
   j. a receiver means intercepting said fifth signal and including:
      A. means for producing a replica of said fourth signal;
      B. first demodulator means for detecting the FM signals produced by said first and second oscillators;
      D. second demodulator means coupled to said first demodulator means for demodulating said FM signals; and
      D. filter means coupled to said second demodulator means for receiving said first and second signals.

10. A system defined by claim 9, wherein said first and second signals lie within a bandwidth of approximately 0–150 Hz and 0–1500 Hz, respectively.

11. A system defined by claim 9, wherein said first and second oscillators have subcarrier frequencies of 2 kHz and 20 kHz, respectively.

12. A system defined by claim 9, wherein said summing means is an amplifier.

13. A system defined by claim 9, wherein said temperature responsive means includes an oscillator whose center frequency is approximately 262 kHz.

14. A system defined by claim 13, wherein said temperature responsive means has a transfer function of approximately 9 Hz shift per °C. change in temperature.

15. A system defined by claim 9, wherein said modulator means comprises an amplitude modulator.

16. A system for propagating a plurality of signals indicative of physiological signals from a point inside a human body to a point external to the body comprising:
   a. first op-amp means responsive to a first physiological stimulus for producing a first signal;
   b. second op-amp means responsive to a second physiological stimulus for producing a second signal;

c. a first oscillator modulated by said first signal and having a frequency dependent on the instantaneous amplitude of said first signal;

d. a second oscillator modulated by said second signal and having a frequency dependent on the instantaneous amplitude of said second signal;

e. said first and second oscillators having two different subcarrier frequencies;

f. shaping means coupled to each of said oscillators for attenuating the odd harmonics present in the frequency modulated (FM) outputs of said first and second oscillators;

g. means for summing the output signals of said shaping means thereby producing a third signal;

h. temperature responsive means for independently of said first and second oscillators producing a fourth signal which varies as a function of temperature;

i. modulator means coupled to the outputs of said summing means and said temperature responsive means for modulating said fourth signal as a function of said third signal thereby producing a fifth signal which contains information of said first, second, and fourth signals;

j. means for propagating said fifth signal to a point external of said human body; and k. receiver means intercepting said fifth signal for separating said first, second, and fourth signals from each other thereby providing means for indicating said physiological stimuli and said body temperature.

17. A system defined by claim 16, wherein said first and second signals lie within a bandwidth of approximately 0–250 and 0–1300 Hz, respectively.

18. A system defined by claim 16, wherein said temperature responsive means includes an oscillator whose center frequency is approximately 262 kHz.

19. A system defined by claim 18, wherein said temperature responsive means has a transfer function of approximately 9 Hz shift per °C. change in temperature.

20. A system defined by claim 16, wherein said modulator means comprises an amplitude modulator.

21. A system for propagating a plurality of signals indicative of measurable variables from an enclosure:

a. first sensor means responsive to a first measurable variable for producing a first signal;

b. second detector means responsive to a second measurable variable for producing a second signal;

c. a first oscillator modulated by said first signal and having a frequency dependent on the instantaneous amplitude of said first signal;

d. a second oscillator modulated by said second signal and having a frequency dependent on the instantaneous amplitude of said second signal;

e. said first and second oscillators having two different subcarrier frequencies;

f. means for summing the output signals of said oscillators thereby producing a third signal;

g. temperature responsive means for independently of said first and second oscillators producing a fourth signal which varies in frequency as a function of temperature;

h. modulator means coupled to the outputs of said summing means and said temperature responsive means for modulating said second signal as a function of said third signal thereby producing a fifth signal which contains information of said first, second, and fourth signals.

i. means for propagating said fifth signal to a point external of said human body; and j. receiver means intercepting said fifth signal for separating said first, second, and fourth signals from each other thereby providing means for indicating said first and second measured variables and said temperature.

* * * * *

UNITED STATES PATENT AND TRADEMARK OFFICE
CERTIFICATE OF CORRECTION

PATENT NO. : 5,415,181
DATED : May 16, 1995
INVENTOR(S) : Hogrefe et al.

It is certified that error appears in the above-indentified patent and that said Letters Patent is hereby corrected as shown below:

Column 8, line 41, delete "D" and insert therefor "C".

Column 10, line 33, substitute "enclosure" for "human body".

Signed and Sealed this

Nineteenth Day of September, 1995

*Attest:*

BRUCE LEHMAN

*Attesting Officer*  *Commissioner of Patents and Trademarks*